United States Patent [19]
Farnum

[11] Patent Number: 6,073,280
[45] Date of Patent: Jun. 13, 2000

[54] RESCUE AND INVALID SUPPORT BELT

[76] Inventor: Randal J. Farnum, 930 W. Eula Ct., Glendale, Wis. 53209

[21] Appl. No.: 09/027,767

[22] Filed: Feb. 23, 1998

[51] Int. Cl.[7] ............................... A61G 1/00; A61G 7/08; A61F 5/37; A61N 1/30
[52] U.S. Cl. .......................... 5/89.1; 5/81.1 T; 128/876; 602/19
[58] Field of Search ................................ 5/81.1 R, 81.1 T, 5/89.1; 294/140; 2/338, 464, 467, 311, 321; 128/96.1, 99.1, 100.1, 101.1; 602/19

[56] References Cited

U.S. PATENT DOCUMENTS

| | | |
|---|---|---|
| 1,035,642 | 8/1912 | Rosse . |
| 1,498,593 | 6/1924 | Waiss . |
| 2,508,795 | 5/1950 | Nielsen . |
| 3,236,234 | 2/1966 | Buckley . |
| 3,896,499 | 7/1975 | Kelly ............................................. 2/311 |
| 3,920,008 | 11/1975 | Lehman ...................... 128/96 |
| 4,139,130 | 2/1979 | Glusker et al. . |
| 4,396,013 | 8/1983 | Hasslinger . |
| 4,449,253 | 5/1984 | Hettinger . |
| 4,538,614 | 9/1985 | Henderson . |
| 4,884,562 | 12/1989 | Stone ........................................ 128/78 |
| 4,981,307 | 1/1991 | Walsh . |
| 5,062,414 | 11/1991 | Grim ........................................ 128/68.1 |
| 5,257,419 | 11/1993 | Alexander ...................................... 2/44 |
| 5,361,418 | 11/1994 | Luzenske . |
| 5,388,274 | 2/1995 | Glover et al. ........................... 2/311 X |
| 5,399,151 | 3/1995 | Smith ......................................... 602/19 |
| 5,514,019 | 5/1996 | Smith . |
| 5,548,843 | 8/1996 | Chase et al. ................................. 2/102 |
| 5,647,378 | 7/1997 | Farnum . |

*Primary Examiner*—Terry Lee Melius
*Assistant Examiner*—James M. Hewitt
*Attorney, Agent, or Firm*—Michael Best & Fredric LLP

[57] ABSTRACT

A support belt and a strap portion includes a strap portion and a pad portion. The pad portion comprising an elongate member having a length sufficient to encircle the body of an individual and a width sufficient to extend from the waist area to the breast area of the individual. A fastener is mounted on the ends of the pad portion for quick attachment and detachment to the individual. The strap portion includes a plurality of straps each having a first part mounted on the outer surface of the pad portion and a second part mounted on the inner surface of the pad portion and in an opposed relation to the first part, stitching extending through the pad portion for securing the first and second strap parts to each other and the pad portion. A part of each of the straps being unfastened and forming a loop to provide handles or anchor point for lifting and pulling the individual.

7 Claims, 3 Drawing Sheets

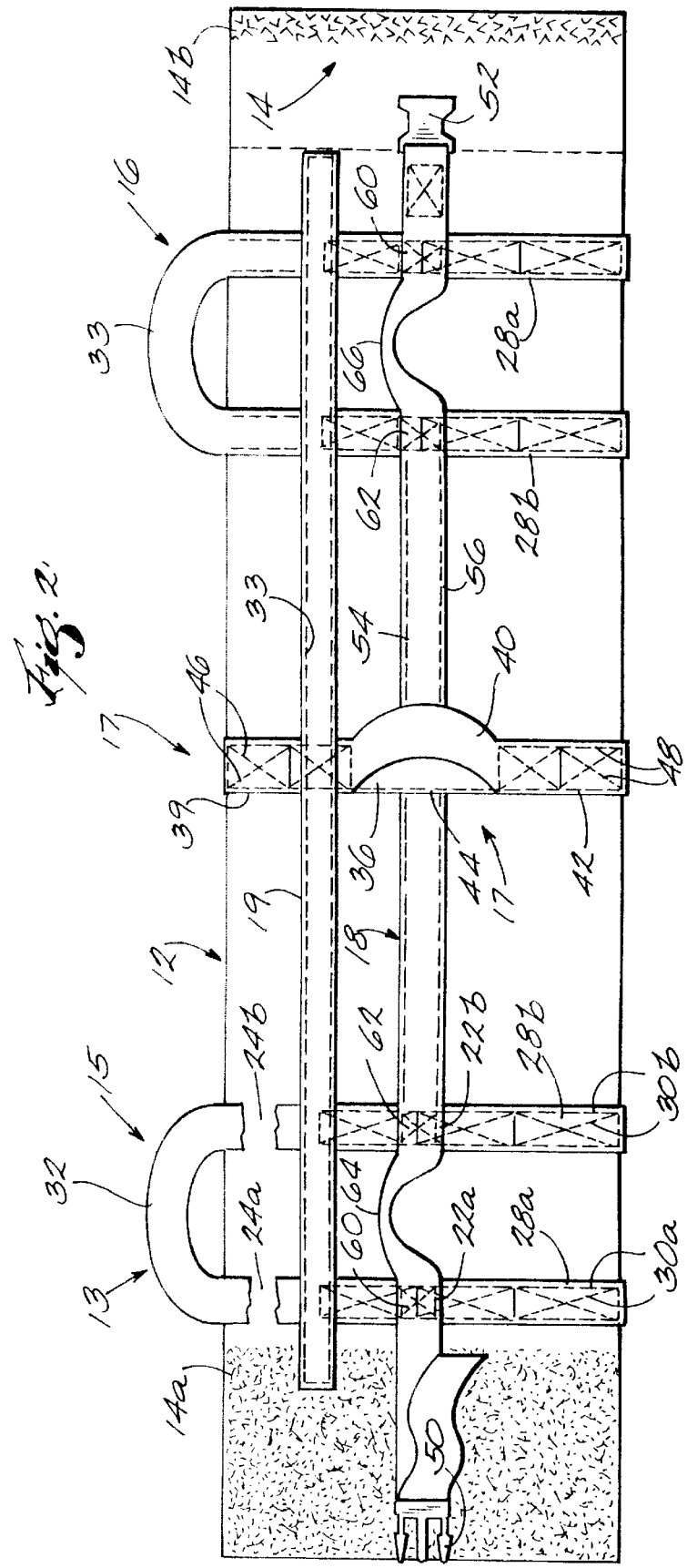

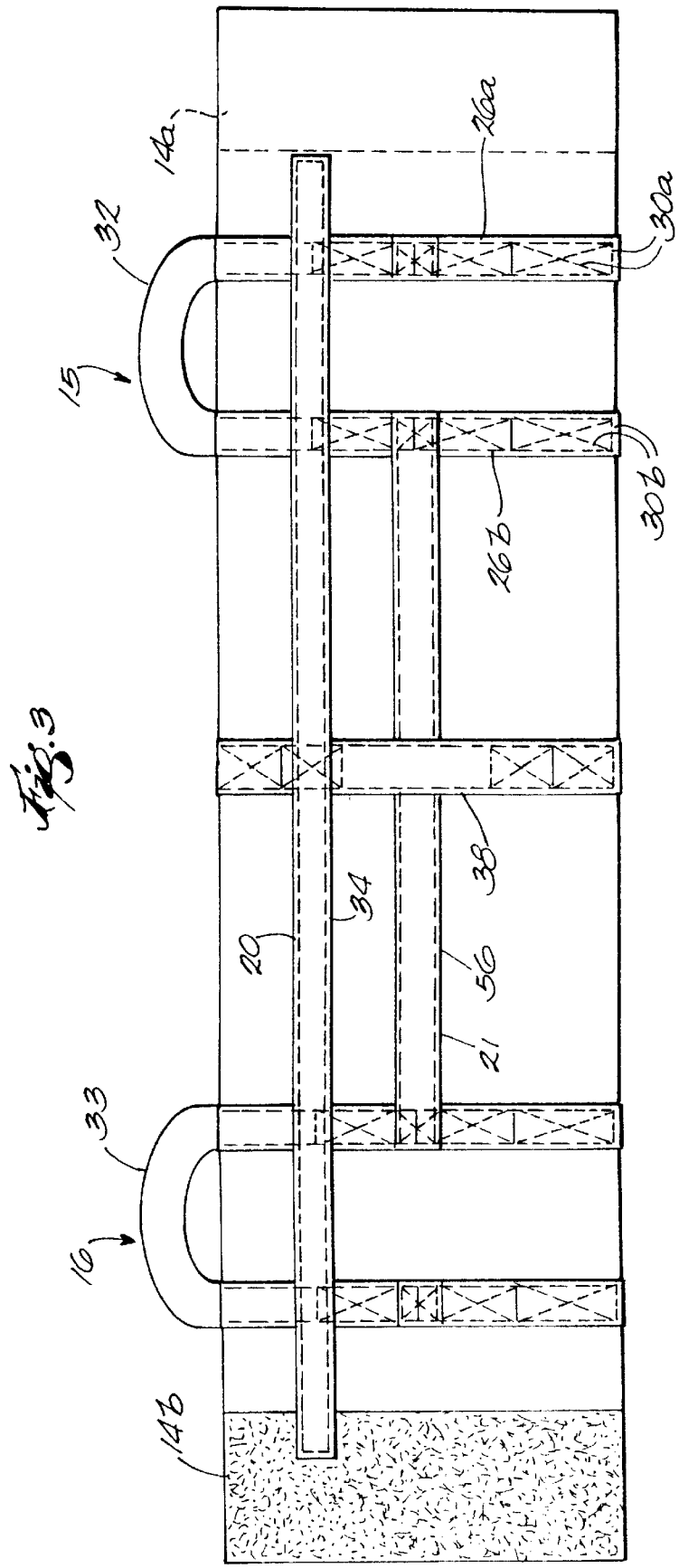

RESCUE AND INVALID SUPPORT BELT

BACKGROUND OF THE INVENTION

This invention relates to rescue and invalid support belts and more particularly to belts for securing and lifting persons in peril or invalids from beds or wheelchairs.

It is often necessary to rescue and remove from harm's way individuals imperilled by accidents, fire or natural disasters. Such persons are often incapacitated, exhausted or otherwise incapable of assisting in their rescue. Therefore, rescue personnel require a means for rapidly securing a victim and for facilitating his movement to a safer location. Prior art rescue belts could not be easily and quickly attached and did not include attachment devices which could withstand significant pulling forces. Moreover, prior art rescue belts were not sufficiently versatile so that they could also readily be used for lifting and stabilizing invalids or incapacitated hospital patients.

SUMMARY OF THE INVENTION

It is an object of the invention to provide a new and improved rescue and invalid support belt.

A further object of the invention is to provide a rescue and invalid lifting belt which can be rapidly attached to an incapacitated individual under less than ideal circumstances.

A further object of the invention is to provide a rescue and patient lifting belt in which lifting forces are not concentrated.

Yet another object of the invention is to provide a rescue and patient lifting belt which can withstand substantial pulling forces.

These and other objects and advantages of the present invention will become more apparent from the detailed description thereof taken with the accompanying drawings.

BRIEF DESCRIPTION OF THE DRAWINGS

FIG. 2 is a front view of the belt according to the invention; and

FIG. 3 is a rear view thereof.

DETAILED DESCRIPTION OF THE PREFERRED EMBODIMENT

Figure 1:
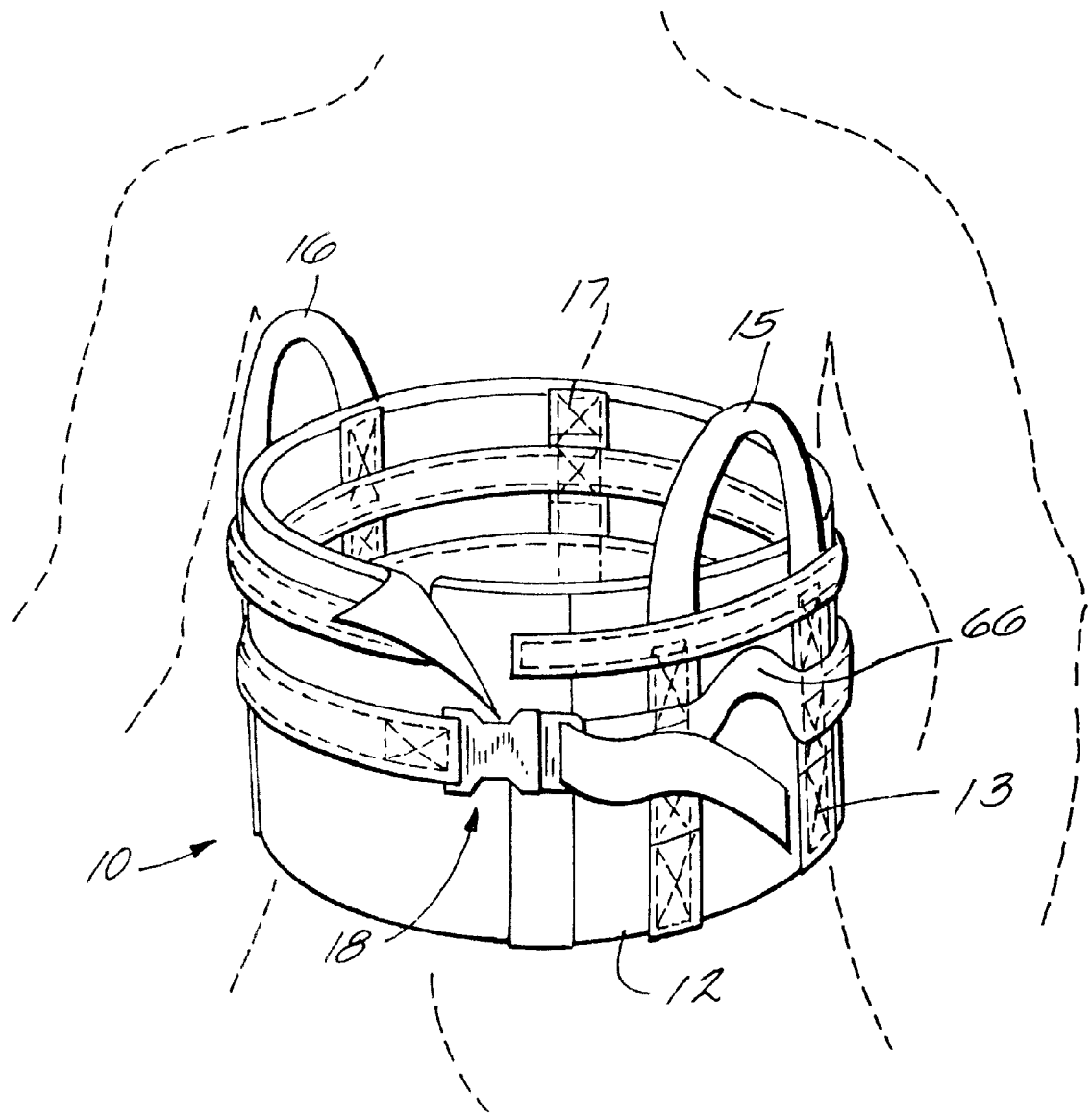
FIG. 1 is a perspective view illustrating how the rescue belt and invalid support belt is worn and used.

The drawings show a rescue and hospital patient lifting and support belt 10 according to the invention to include a pad portion 12 which is generally rectangular in plan view and a strap portion 13. The pad portion 12 is formed of a flexible and elastic material. One example of a material which may be used for the pad portion 12 is a closed cell neoprene rubber such as that sold under the trademark RUBATEX by Rubatex Corporation. For aesthetic purposes, the outer surface of the pad portion 12 may be covered by a flexible material, such as Lycra. However, to minimize the possibilities of the belt 10 slipping during use, the inner surface is preferably not covered.

The opposite ends of the pad portion 12 includes at least one fastener so that the ends may be joined about the chest of the user as shown in FIG. 1. In the preferred embodiment, the fastener comprises a hook and loop fastener 14 sold under the trademark Velcro and including a hook strip 14a and a loop strip 14b.

The length of the pad portion 12 should be such that it fits snugly about the user without discomfort. It will be appreciated that different sizes are required to fit different sized individuals. Preferably, the width of the pad portion 12 is such that it extends approximately from the waist to the breast area of the wearer. A typical width would be about ten inches.

The strap portion 13 includes a plurality of straps which are connected to each other and to the pad portion 12 to provide a series of handles or anchor points which can withstand substantial pulling forces without separation. The individual straps which form the strap portion comprise heavy duty webbing strips of a flexible material, such as, nylon or cotton webbing. In the preferred embodiment, the strap portion 13 includes a pair of side handle straps 15 and 16, a rear handle strap 17, a body strap 18 and anchor straps 19, 20 and 21.

The side handle straps 15 and 16 each preferably comprises a single strip of heavy duty webbing and are identical so only handle strap 15 will be discussed in detail for the sake of brevity. In the illustrated embodiment, the two ends of the single piece of webbing which forms the handle strap 15 are positioned in spaced apart relation at points 22a and 22b on the front surface of the pad portion 12. The webbing extends upwardly from points 22a and 22b and around the upper edge of the pad 12 to define segments 24a and 24b. The webbing material continues downwardly in a parallel spaced apart relation along the back of the pad 12 to define segments 26a and 26b as shown in FIG. 3, around the lower edge of the pad portion 12 and upwardly along the front surface in a parallel spaced apart relation to a point above points 22a and 22b to define segments 28a and 28b as seen in FIG. 2. Stitching 30a and 30b secures webbing portions 24a and 28a to portion 26a and portions 24b and 28b to portion 26b. Portions 32 and 33 of handle straps 15 and 16, respectively, are unattached and longer than the gap between the stitched portions to define lifting handles. It can be seen that the handle straps 15 and 16 each completely surrounds the pad portion 12 in two places and each is secured to itself with the pad portion 12 disposed therebetween. In addition, anchor straps 19 and 20 are secured by stitching 34 respectively to the front and rear surfaces of the pad 12 and in an opposed relation and extending perpendicularly to the handle strap portions 24a, 24b and over the initial points 22a and 22b. As a result when force is applied to either of the handles 32 and/or 33, the stress is transmitted to the relatively strong webbing portions secured on the opposite sides of the pad portion 12 and to the anchor straps 19 and 20 while stress on the relatively weaker pad portion 12 is minimized.

The rear handle strap 17 also comprises a single piece of heavy duty webbing material which, in the illustrated embodiment, having one end fixed at about the upper edge of the front surface of pad portion 12 and extending downwardly along the front surface equidistantly between and parallel to the handle straps 15 and 16 to define a first portion 36 as seen in FIG. 2. The webbing material extends around the lower edge of the pad 12 upwardly along the back surface as seen in FIG. 3 to define portion 38, around the upper edge and downwardly over the upper portion of segment 36 to define a portion 39. There is then an unattached portion 40 which is unsecured and a lower portion 42 which terminates at the lower end of the pad portion 12. The unattached portion 40 is longer than the gap between the portions 39 and 42 to define a loop or handle. Stitching 44 secures the portion 36 on the front face of pad 12 to the portion 38 on the back surface while stitching 46 secures the portion 39 to the portions 36 and 38 and stitching 48 secures the portion 42 to the portions 36 and 38. It can be seen that, the handle formed by the portion 40 is secured to a continuous piece of webbing material which surrounds the pad portion 12 and is in addition secured to the anchor straps 19, 20 and 21.

The body strap 18 also preferably consists of a single strip of heavy duty webbing material having quick release buckle portions 50 and 52 at its opposite ends. The center portion 54 of body strap 18 extends between portions 28b of side handle strap 15 and 16 and beneath the portion 36 of rear handle strip 17 and is secured to the pad portion 12 and anchor strap 21 by stitching 56. The strap 18 is also anchored by stitching 60 and 62 to the legs 28a and 28b, respectively, of handle strap 15 and 16. The length of the strap 18 between these anchor points is longer than the distance between the legs of the straps 15 and 16 to define additional handles 64 and 66. The anchor strap 21 is also secured by stitches 56 to the rear surface of pad 12 and in an opposed relation and of equal length to that portion 54 of the strap 18 between portions 28b of handle straps 15 and 16. The body strap 18 is attached both to the straps 15 and 16, strap 17 and anchors straps 19, 20 and 21.

The illustrated embodiment provides a series of interconnected straps 15, 16, 17, 18, 19, 20 and 21 which surround the individual and provide mutual support. While the straps 15, 16, 17 and 18 are preferably each formed by a single strip of webbing material for strength, each may also be formed of two or more pieces, which, however, would result in a reduction of overall strength. The stitching 30a, 30b, 33, 36, 44, 46, 48, 56, 60, and 62 comprises a fastening for securing the strap portions to each other and to the pad portion 12. It will be appreciated that other suitable fasteners, such as rivets or staples may also be employed, although stitching is preferred.

When in use, the support belt 10 can rapidly be attached to an individual by encircling the pad 12 about the body and securing the hook and loop fastener 14, after which, the buckle 50, 52 is closed. This secures the belt 10 in place. Because the inside surface of the pad 12 is of a rubber or rubber-like material, it provides frictional engagement with respect to the wearer's garments or skin so that the belt resists slipping. In a rescue situation, the rescuer may attach a hook or the like to one or more of the handles 32, 33, 40, 64 or 66 so that the periled individual may be hauled to safety. Because of the high strength of the interlocking webbing strips, a substantial pulling force can be exerted without failure. Similarly, when the belt 10 is employed with an incapacitated patient, the handles 32, 33, 64 and 66 provide anchor points or handles which permit the patient to be lifted. In addition, the rear handle 40 permits a handle for stabilizing and supporting the patient while walking.

The relatively large width of the belt portion 12, which extends from the wearer's hips to the breast area, provides more surface area contact to insure stability for safety and is less likely to cause injury or discomfort by distributing the weight of an individual over a large area. This minimizes the amount of twisting when the individual is lifted and minimizes torquing and binding. Moreover, the exposed inner surface of the belt portion 12 minimizes the possibility of slippage to increase patient comfort and safety. Also because the belt portion 12 is resilient and may be easily stretched, it readily conforms to the patient's body to provide comfort and support.

While only a single embodiment of the invention has been illustrated and described, it is not intended to be limited thereby but only by the scope of the appended claims.

I claim:

1. A support belt including a pad portion having an inner surface for engaging an individual and an outer surface, said pad portion comprising an elongate member having ends and a length sufficient to encircle a body of an individual, said pad portion having opposite side edges which define a width sufficient for extending from a waist area to a breast area of the individual, a fastener mounted on the ends of the pad portion for quick attachment and detachment to the individual, first, second and third spaced apart strap portions, each strap portion including a first part mounted on the outer surface of the pad portion and a second part mounted on the inner surface of the pad portion, the first and second parts of each strap portion being disposed in a parallel opposed relation on opposite sides of the pad portion, said first strap portion extending for at least a substantial portion of the length of the pad portion and spaced from the opposite edges thereof, the second and third strap portions being spaced apart from each other and intersecting said first strap portion intermediate their ends and at points spaced from the opposite side edges of the pad portion, fastening means engaging the first and second strap parts of each of said strap portions and extending through the pad portion for securing each of said first and second strap parts of each strap portion to each other and to the pad portion and for securing said second and third strap portions to said first strap portion, a gap in the fastening means engaging the first part of said second and third strap portions, a portion of the first part of said second and third strap portions spanning the gap in the fastening means and being longer than a distance across the gaps in the fastening means to define loops for providing handles or anchor points for lifting and manipulating an individual.

2. The belt set forth in claim 1 and including a fourth strap portion disposed between said second and third strap portions and intersecting said first strap portion, said fourth strap portion including first and second parts disposed on the opposite sides of the pad portion, said fourth strap portion intersecting said first strap portion at a point spaced from the opposite side edges of the pad portion, and including means for securing the first and second parts of the fourth strap portion to each other and to opposite sides of the pad portion and to the first strap portion, a gap in a central portion of the means for securing the first part of the fourth strap portion to define a loop in the first part of the fourth strap portion, the second and third strap portions being disposed at sides of a wearer of the support belt when the support belt is attached and the fourth strap portion being disposed in a rear of a wearer of the support belt.

3. A support belt including a pad portion having an inner surface for engaging an individual and an outer surface, said pad portion comprising an elongate member having ends and a length sufficient to encircle a body of an individual and having a width sufficient for extending from a waist area to a breast area of an individual, a fastener mounted on the ends of the pad portion for quick attachment and detachment to an individual, first, second and third spaced apart strap portions, each strap portion including a first part mounted on the outer surface of the pad portion and a second part mounted on the inner surface of the pad portion, the first and second parts of each strap portion being disposed in a parallel opposed relation on opposite sides of the pad portion, said first strap portion extending for at least a substantial portion of the length of the pad portion, the second and third strap portions being spaced apart from each other and intersecting said first strap portion, fastening means engaging the first and second strap parts of each of said strap portions and extending through the pad portion for securing each of said first and second parts of each strap portion to each other and to the pad portion and for securing said second and third strap portions to said first strap portion, a gap in the fastening means engaging the first part of at least one of the strap portions, a portion of the first part of at least one of the strap portions spanning the gap in the fastening means being longer than a distance across the gap to define a loop for providing a handle or anchor point for lifting and manipulating an individual, a gap in the fastening means engaging the first part of the second and third strap portions, portions of said first strap parts of the first and second strap portions spanning said gaps in the second and third strap portions being longer than said gaps to define a pair of spaced loops for providing spaced handle or anchor points, a fourth strap portion disposed between said second and third strap portions and intersecting said first strap portion, said fourth strap portion including first and second parts disposed on opposite sides of the pad portion, said fourth strap portion intersecting said first strap portion, and including means for securing the first and second parts of the fourth strap portion to each other and to opposite sides of the pad portion and to the first strap portion, the second and third strap portions being positioned at opposite sides and the fourth strap portion being positioned behind a wearer of the support belt when the fastener is fastened, a gap in the fastening means engaging the first part of the fourth strap portion, a portion of the first part of the fourth strap portion spanning the gap and being longer than the gap to define a handle or anchor loop between the second and third strap portions.

4. A support belt including a pad portion having an inner surface for engaging an individual and an outer surface, said pad portion comprising an elongate member having ends and a length sufficient to encircle a body of an individual and having a width sufficient for extending from a waist area to a breast area of the individual, a fastener mounted on the ends of the pad portion for quick attachment and detachment to an individual, first, second and third spaced apart strap portions, each strap portion including a first part mounted on the outer surface of the pad portion and a second part mounted on the inner surface of the pad portion, the first and second parts of each strap portion being disposed in a parallel opposed relation on opposite sides of the pad portion, said first strap portion extending for at least a substantial portion of the length of the pad portion, the second and third strap portions being spaced apart from each other and intersecting said first strap portion, fastening means engaging the first and second parts of each of said strap portions and extending through the pad portion for securing each of said first and second parts of each strap portion to each other and to the pad portion and for securing said second and third strap portions to said first strap portion, a gap in the fastening means engaging the first part of at least one of the strap portions, a portion of the first part of at least one of the strap portions spanning the gap in the fastening means and being longer than a distance across the gap to define a loop for providing a handle or anchor point for lifting and manipulating an individual, a gap in the fastening means engaging the first part of the second and third strap portions, portions of said first strap parts of the first and second strap portions spanning the gaps in the fastening means engaging the second and third strap portions being longer than said gap to define a pair of spaced loops for providing spaced handle or anchor points, a fourth strap portion disposed between said second and third strap portions and intersecting said first strap portion, said fourth strap portion including first and second parts disposed on the opposite sides of the pad portion, said fourth strap portion intersecting said first strap portion, and including means for securing the first and second parts of the fourth strap portion to each other and to opposite sides of the pad portion and to the first strap portion, the second and third strap portions being disposed at opposite sides and the fourth strap portion is positioned to be disposed behind a wearer of the support belt when the fastener is fastened, a body strap portion having ends and a length, said body strap portion including a first part disposed on the outer surface of the pad portion and extending perpendicularly to the second, third and fourth strap portions, a quick release buckle mounted at the ends of said body strap portion for securing the support belt to an individual, said body strap portion also including a second part disposed on the inner surface of the pad portion and in an opposed relation to the first part of the body strap portion, and fastening means fastening the first and second parts of the body strap portion to each other and to each of the second, third, and fourth strap portions wherein each of the strap portions are fastened to each other and to the pad portion.

5. The belt set forth in claim 4 and wherein there are a pair of gaps in the fastening means engaging the first part of the body strap portion, the length of the first part of the body strap portion across the gap being longer than the gap to define two additional handles or anchoring loops.

6. A support belt including a pad portion having an inner surface for engaging an individual and an outer surface, said pad portion comprising an elongate member having ends and a length sufficient to encircle a body of an individual and having a width sufficient to extend from a waist area to a breast area of an individual, a fastener mounted on the ends of the pad portion for quick attachment and detachment to the individual, first, second and third handle strap portions disposed in a spaced apart relation, each handle strap portion having a first part mounted on the outer surface of the pad portion and a second part on the inner surface thereof and in an opposed relation to the first part, and fastening means for securing each of the first and second parts of the strap portions to each other and to the pad portion, a sub part of each of the first parts of the strap portions being unfastened and forming a loop to provide a handle or anchor point, the first and second handle strap portions being disposed at a side when the support belt is worn by an individual and said third handle strap portion being disposed between the first and second handle strap portions and behind an individual, an anchor strap portion having a first part mounted on the inner surface of the pad portion and a second part mounted on the outer surface of said pad portion and each intersecting each of said handle strap portions, fastening means engaging the first and second parts of the anchor strap portion and the handle strap portions for securing the anchor strap portion to the pad portion and to the handle strap portions, a body strap portion, said body strap portion having ends and including a first part disposed on the outer surface of the pad portion and extending perpendicularly to the first, second and third handle strap portions, a quick release buckle means at the ends of the body strap portion for securing the support belt to an individual, said body strap portion also including a second part disposed on the inner surface of the pad portion and in an opposed relation to the first part, and fastening means fastening the first and second parts of the body strap portion to each other and to each of the first, second and third handle strap portions wherein each of the strap portions are fastened to each other and to the pad portion.

7. A support belt including a pad portion having an inner surface for engaging an individual and an outer surface, said pad portion comprising an elongate member having ends and a length sufficient to encircle a body of an individual, said pad portion having opposed side edges which define a width sufficient for extending from a waist area to a breast area of an individual, a fastener mounted on the ends of the pad portion for quick attachment and detachment to an individual, first, second and third handle strap portions disposed in a spaced apart relation, each handle strap portion having a first part mounted on the outer surface of the pad portion and a second part on the inner surface of the pad portion and in an opposed relation to the first part, fastening means for securing each of the first and second parts of the handle strap portions to each other and to the pad portion, a sub part of each of the first parts of the handle strap portions being unfastened and forming a loop to provide a handle or anchor point, the first and second handle strap portions being disposed at a side when the support belt is worn by an individual and the third handle strap portion being disposed between the first and second handle strap portions and at a rear of an individual, an anchor strap portion spaced from the opposed side edges and having a first part mounted on the inner surface of the pad portion and a second part mounted on the outer surface of said pad portion and each intersecting each of the handle strap portions at points between the opposed side edges of the pad portion, a fastening means engaging the first and second parts of the anchor strap portion and the handle strap portions for securing the anchor strap portion to the pad portion and to the handle strap portions.

* * * * *